United States Patent [19]
Leonardi et al.

[11] Patent Number: 5,453,518
[45] Date of Patent: Sep. 26, 1995

[54] FLAVONE DERIVATIVES

[75] Inventors: Amedeo Leonardi, Milan; Gianni Motta, Barlassina; Carlo Riva, Varese; Luciano Guarneri, Garbagnate Milanese, all of Italy

[73] Assignee: Recordati S.A., Chemical and Pharmaceutical Company, Chiasso, Switzerland

[21] Appl. No.: 45,420

[22] Filed: Apr. 9, 1993

[30] Foreign Application Priority Data

Apr. 10, 1992 [IT] Italy ................... MI92A0884

[51] Int. Cl.$^6$ ............... C07D 311/22; C07D 339/08; A61K 31/35; A61K 31/385
[52] U.S. Cl. ............................... 549/403; 549/21
[58] Field of Search ............... 549/21, 403; 514/436, 514/451

[56] References Cited

U.S. PATENT DOCUMENTS

| | | | |
|---|---|---|---|
| 2,921,070 | 1/1960 | Da Re | 544/151 |
| 3,277,094 | 10/1966 | Werner | 544/394 |
| 3,350,411 | 10/1967 | Da Re | 549/403 |
| 3,810,896 | 5/1974 | Witte et al. | 544/376 |
| 4,089,969 | 5/1978 | Muchowski et al. | 514/416 |
| 4,495,198 | 1/1985 | Wu | 514/456 |

(List continued on next page.)

FOREIGN PATENT DOCUMENTS

| | | |
|---|---|---|
| A38591/93 | 2/1994 | Australia . |
| 0072620 | 7/1982 | European Pat. Off. . |
| 0064165 | 11/1982 | European Pat. Off. . |
| 0081621 | 6/1983 | European Pat. Off. . |

(List continued on next page.)

OTHER PUBLICATIONS

Atassi et al., *Eur. J. Med. Chem.*, 20:393–402 (1985).
Augstein et al., *J. Med. Chem.*, 8:356–367 (1965).
Bagli, *J. Med. Chem.*, 19:876–882 (1976).
Bonte et al., *Eur. J. Med. Chem.* 25:361–368 (1990).
Carroll et al., *J. of Med. Chem.*, 19(9):1111–1119(1976).

(List continued on next page.)

*Primary Examiner*—C. Warren Ivy
*Assistant Examiner*—D. Margaret M. Mach
*Attorney, Agent, or Firm*—Darby & Darby

[57] ABSTRACT

A compound of the general formula:

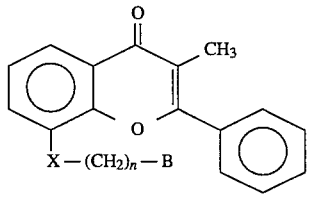

wherein X represents —CO—, —COO—, —CONH—, —CON(CH$_3$)—, —CH$_2$NH—, —CH$_2$N(CH$_3$)—, —CH$_2$NHCO—, —CH$_2$N(CH$_3$)CO—, —CH$_2$O—, —CH$_2$S—, —CH$_2$SO—, or —CH$_2$SO$_2$—; n represents an integer from 1 to 4; and B represents one of the following groups:

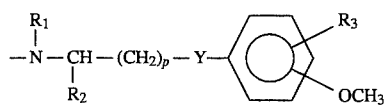

wherein R$_1$ represents a lower alkyl (C$_1$–C$_4$) group; R$_2$ represents a hydrogen atom or a lower alkyl (C$_1$–C$_4$) group; R$_3$ represents a hydrogen atom or OR$_4$ group wherein R$_4$ represents a lower alkyl (C$_1$–C$_4$) group; p represents an integer from 1 to 3; and Y represents a valence bond (Y1), or one of the following groups:

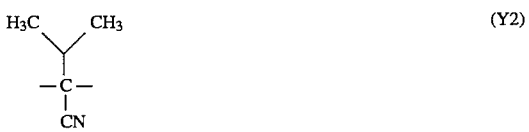

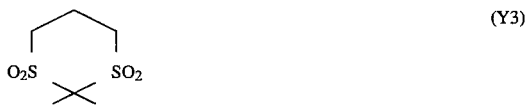

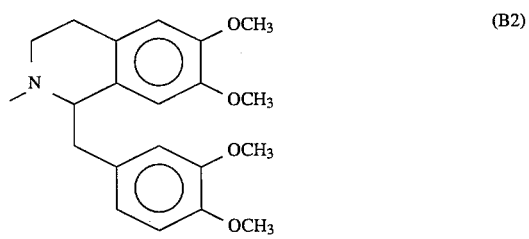

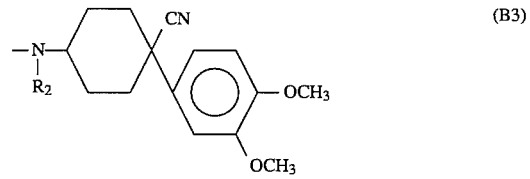

wherein R$_2$ is as above defined as well as the enantiomers, diastereomers, N-oxides, prodrugs, metabolites, prodrugs of metabolites, and pharmaceutically acceptable salts of these compounds. The compounds are long-lasting antispasmodic therapeutic agents and are particularly useful for the treatment of lower urinary tract disorders.

10 Claims, No Drawings

U.S. PATENT DOCUMENTS

| | | | |
|---|---|---|---|
| 4,539,318 | 9/1985 | Baldwin et al. | 514/227.8 |
| 4,668,804 | 5/1987 | Wu | 549/403 |
| 4,668,805 | 5/1987 | Wu | 549/403 |
| 4,684,651 | 8/1987 | Kikumoto et al. | 514/253 |
| 4,797,498 | 1/1989 | Albrecht et al. | 549/403 |
| 4,940,711 | 7/1990 | Nardi et al. | 514/255 |
| 5,091,182 | 2/1992 | Ong et al. | 424/400 |

FOREIGN PATENT DOCUMENTS

| | | |
|---|---|---|
| 0100250 | 2/1984 | European Pat. Off. . |
| 0104614 | 4/1984 | European Pat. Off. . |
| 0108986 | 5/1984 | European Pat. Off. . |
| 0107804 | 5/1984 | European Pat. Off. . |
| 0206802 | 12/1985 | European Pat. Off. . |
| 0190015 | 8/1986 | European Pat. Off. . |
| 0288077 | 12/1987 | European Pat. Off. . |
| 0270342 | 6/1988 | European Pat. Off. . |
| 0333676 | 9/1989 | European Pat. Off. . |
| 0343961 | 11/1989 | European Pat. Off. . |
| 0364350 | 4/1990 | European Pat. Off. . |
| 0372305 | 6/1990 | European Pat. Off. . |
| 0430693 | 6/1991 | European Pat. Off. . |
| 0571243A1 | 11/1993 | European Pat. Off. . |
| 0435749 | 7/1991 | France . |
| 0401653 | 12/1990 | Germany . |
| 1166595 | 10/1969 | United Kingdom . |
| 2161807 | 1/1986 | United Kingdom . |
| 2193633 | 2/1988 | United Kingdom . |
| WO91/18597 | 12/1991 | WIPO . |
| WO92/01681 | 2/1992 | WIPO . |

OTHER PUBLICATIONS

Cunico et al., *Org. Chem.*, 48:2780–2782(1983).
Da Re, *Ann. Chim.* pp. 506–513 (1962).
Da Re et al., *Eur. J. Med. Chem.*, 13:387–388 (1987).
Da Re et al., *J. Med. Chem.*, 2(3):263–269 (1960).
Engel et al., *J. Med. Chem.*, 33:2976–2981 (1990).
Frishman et al., *Cardiovascular Pharmacotherapy II*, 72(2):427–440 (1988).
Garcia—Sainz et al., *Biochemical and Biophysical Research Communications*, 186(2):760–767(1992).
Gartside et al., *European Journal of Pharmacolgy*, 191:391–400 (1900).
Grewal et al., *J. Pharmac. Exp. Therap.*, 160(2):268–276 (1968).
Hamon et al., *Annals New York Academy of Sciences*, pp. 114–131 (1990).
Hartig et al., *Drug Delivery Res.*, 26(3):215–224 (1992).
Laubie et al., *Arzheim–Forsch*, 19:1820–1826 (1969).
Leclerc et al., *Arzheim–Forsch Drug. Res.*, 35:1357–1367 (1985).
Mielke et al., *Curr. Therap. Res.*, 15:(6):324–326 (1973).
Mull et al, *J. Med. Chem.*, 8:332–338 (1965).
Overberger et al., *J.A.C.S.*, 71:2661–2666 (1949).
Perez et al., *Molecular Pharmacology*, 40:876–883 (1991).
Ratouis et al., *J. Med. Chem.*, 8:271–273 (1965).
Ratouis et al., *J. Med. Chem.*, 8:104–107 (1965).
Romero et al., *Annual Reports in Medical Chemistry*, 27(3):21–30 (1992).
Saari et al., *J. Med. Chem.*, 33:97–101 (1990),
Silvestrini et el., *Arzheim–Forsch./Drug. Res.*, 32:668–673 (1982).
Traber et al., *TIPS*, 8:432–437 (1987).
Uneyama et al., *Bull. Chem. Soc. Jpn.*, 58:2361–2365 (1985).
Valenti et al., *Boll. Chim. Farm.*, 114:294–300 (1975).
Vizi et al., *Medicinal Research Reviews*, 6:431–449 (1986).
Wu et al., *J. Med. Chem.*, 35:3519–3525 (1992).
Zifa et al., Pharmacological Reviews, 44(3):401–458 (1992).
*Drugs of the Future*, 6:346–347 (1981).
*Chemical Abstracts* 55:5534a (1959).
*Chemical Abstracts* 59:2832b (1963).
*Chemical Abstracts* 63:11589h (1965).
*Chemical Abstracts* 66:3769s (1967).
*Chemical Abstracts* 66:85664e (1967).
*Chemical Abstracts* 67:64435m (1967).
*Chemical Abstracts* 76:14577z (1972).
*Chemical Abstracts* 78:584606 (1973).
*Chemical Abstracts* 98:107161d (1983).
*Chemical Abstracts* 83:131584c (1975).
*Chemical Abstracts* 84:59400u (1976).
*Chemical Abstracts* 100:103390q (1984).
*Chemical Abstracts* 104:109686v (1985).
*Chemical Abstracts* 104:19499g (1985).
*Chemical Abstracts* 105:78821z (1986).
*Chemical Abstracts* 107:236661v (1987).
*Chemical Abstracts* 108:15674v (1988).
*Chemical Abstracts* 108:37647r (1988).
*Chemical Abstracts* 108:150298r (1988).
*Chemical Abstracts* 109: 128816g (1988).
*Chemical Abstracts* 110:135063h (1989).
*Chemical Abstracts* 111:153607p (1989).
*Chemical Abstracts* 112:216577x (1990).
*Chemical Abstracts* 113:109332n (1990).
*Chemical Abstracts* 116:262282c (1992),
*Chemical Abstracts* 59:10006g (1963).

FLAVONE DERIVATIVES

The invention relates to flavone amino derivatives and to the pharmaceutical compositions containing them.

BACKGROUND OF THE INVENTION

Urinary incontinence is a pathological condition which affects an increasing number of elderly people and is presently treated with anticholinergic-spasmolytic drugs. One of these drugs, which differentiates itself for a practical absence of anticholinergic effects, is 8-(2-(N-piperidino)ethoxycarbonyl)-3-methyl-4-oxo-2-phenyl-4H-1-benzopyran, the formula of which is:

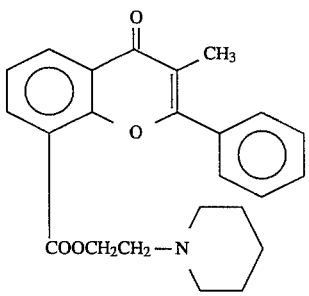

commonly known as flavoxate.

However, a problem associated with the use of this drug is its low stability in physiological fluids.

The compounds which are an object of this invention are also flavone derivatives essentially having methoxyphenyl-substituted complex amino functions in place of the piperidino group present in the flavoxate structure. Another structural variation of the compounds which are an object of the present invention involves substitutions of the ethoxycarbonyl group which separates the amino moiety from the benzopyran ring. Surprisingly, the compounds of the invention were found to have a powerful antispasmodic action and, also, to be considerably more stable at a physiological pH than flavoxate, so that their half-lives are considerably longer than that of flavoxate. Therefore, these properties make their use as long-lasting antispasmodic drugs indicated, particularly with respect to the treatment of lower urinary tract disorders, without, however, limiting their therapeutic use to this field.

SUMMARY OF THE INVENTION

The compounds of the invention have the general formula I:

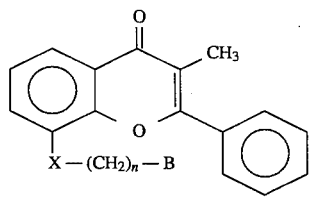

where

X is one of the following groups, each of which is shown intending the left end to be the end linked to the benzopyran ring and the right end to be the end linked to the alkylene chain:

(X1) —CO—,
(X2) —COO—,
(X3) —CONH—,
(X4) —CON(CH$_3$)—,
(X5) —CH$_2$NH—,
(X6) —CH$_2$N(CH$_3$)—,
(X7) —CH$_2$NHCO—,
(X8) —CH$_2$N(CH$_3$)CO—,
(X9) —CH$_2$O—,
(X10) —CH$_2$S—,
(X11) —CH$_2$SO—, and
(X12) —CH$_2$SO$_2$—, n is an integer from 1 to 4; and
B is one of the following groups:

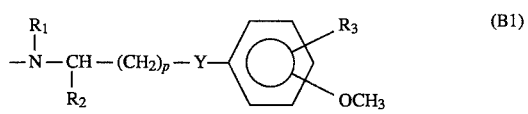

where $R_1$ is a lower alkyl ($C_1$–$C_4$) group; $R_2$ is a hydrogen atom or a lower alkyl ($C_1$–$C_4$) group; $R_3$ is a hydrogen atom or $OR_4$ wherein $R_4$ is a lower alkyl ($C_1$–$C_4$), preferably a methoxy group; p is an integer from 1 to 3; and Y is a valence bond (Y1), or one of the following groups:

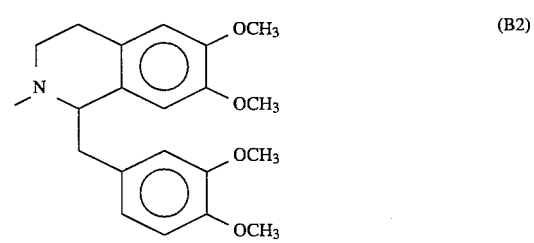

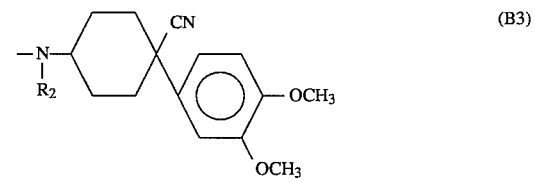

wherein $R_2$ is as defined above.

The present invention includes also the enantiomers, diastereoisomers, N-oxides, and pharmaceutically acceptable salts of these compounds as well as pro-drugs, e.g., compounds which break down into formula I compounds as well as metabolites of formula I compounds or pro-drugs thereof which have the same type of activity, i.e., antispasmodic action although not necessarily to the same degree.

As defined herein, prodrugs of formula I compounds refer to derivatives of formula I compounds bearing reactive groups such as NH (such as that contained in $X_5$) prepared for various purposes, e.g., to improve the pharmaco-kinetic properties (adsorption, distribution, metabolism, plasmatic half-life, etc.) of the formula I compounds. When formula I compounds are administered to mammals as a prodrug or "masked" form, the formula I compounds are liberated and exert their pharmacological action in mammals receiving them. Examples of these prodrug derivatives have the following structure (Formula I compound) —N—C (O,S) —W—F wherein W is a bond, an oxygen or sulfur atom, or a NH group, F represents alkyl groups, optionally containing hetero atoms such as O, S, N or substituted nitrogen, carbocyclic groups or heterocyclic groups, optionally substituted with amino, alkylamino, dialkylamino, dialkylaminoalkyl, carboxy, alkoxycarbonyl, carboxamido.

Preferably W is a bond and F is $CH_3$, $(CH_3)_3C$, $CH_3(CH_2)_3$, B'-$CH_2$-phenyl, B'-alkyl, B'-CO-alkyl, HOCO-alkyl, alkyl-OCOalkyl, where B' represents a dialkylamino group or a cyclic amino group, optionally containing other heteroatoms such as N, O or S.

Other examples of prodrug derivatives are those obtained by the derivatization of "acidic" NH groups (Ny) such as those present in X3 and X7, yielding derivatives having the formula:

(Formula I Compound) —Ny—CH(J) —O—C (O,S) —W—F wherein J represents hydrogen atom or alkyl group, phenyl or trichloromethyl group and W and F have the same meaning and preferred meaning as described above.

Additional prodrug examples are derivatives of the formula:

(Compound I) —Ny—$CH_2$—B' wherein B' represents a dialkylamino group or a cyclic amino group, optionally containing other heteroatoms such as N, O or S.

Additional objects of the present invention are the pharmaceutical compositions which include said compounds, or any enantiomers, diastereoisomers, N-oxides or pharmaceutically acceptable salts of said compounds, prodrugs, metabolites of formula I compounds, or prodrugs of formula I metabolites in association with pharmaceutically acceptable diluents or carriers.

The administerable pharmaceutical composition may take the form of oral tablets, vaginal or uterine tablets or suppositories, pills, capsules, liquid solutions, suspensions, nasal sprays or the like, preferably in unit dosage forms suitable for simple administration of precise dosages.

These pharmaceutical compositions may be formulated to include conventional non-toxic solid carriers such as pharmaceutical grades of mannitol, lactose, starch, magnesium stearate, sodium saccharin, talcum, cellulose, glucose, gelatin, sucrose, magnesium carbonate and the like.

The active compound as defined above may also be formulated as suppositories using, for example, semisynthetic triglycerides or polyalkylene glycols (e.g., polyethylene glycol) as the carrier. Liquid pharmaceutically administrable compositions may be prepared, for example, by dissolving or dispersing, the inventive compound and optional pharmaceutical adjuvants in a carrier such as water saline, aqueous dextrose, glycerol, or ethanol to form a solution or suspension. If desired, the pharmaceutical composition may also contain minor amounts of nontoxic auxiliary substances such as wetting agents, emulsifying agents and pH buffering agents. Representative examples include sodium acetate, sorbitan monolaurate and triethanolamine oleate.

Actual methods of preparing such dosage forms are known, or will be apparent, to those skilled in this art. See, for example, Remington's "Pharmaceutical Sciences," Mack Publishing Company, Easton, Pa., 18th Ed. (1990).

The composition or formulation to be administered preferably contains a quantity of the active compound(s) in an amount effective to achieve a therapeutic effect. Generally, an oral daily dose ranging from 10 to 100 mg of the active compound may be administered, with administration being a single daily dose or up to three or four smaller dosages regularly given throughout the day. The amount of active compound administered will, of course, depend on its relative activity. In the case of i.v. administration, a daily dose generally ranges from 0.5 to 5 mg of the active compound.

The 3-methyl-4-oxo-2-phenyl-4H-1-benzopyran-8-yl group shall be hereinafter abbreviated to Fl.

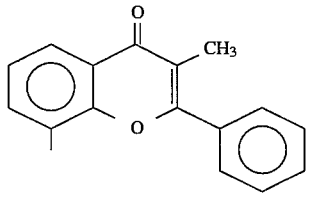

The alphanumerics X1 through X12, B1 through B3 and Y1 through Y3 shall be used as abbreviations for the groups X, B and Y to which they are respectively applied above. B1 and B3 represent all the variants of their respective groups. If a specific substitution pattern is intended for group B1, it shall be shown as B1($R_1$, $R_2$, p, Y, a), where a is the substitution position of the methoxy group in the benzene ring, when $R_3$=H, or as B1($R_1$, $R_2$, p, Y, a, b), where a and b are the substitution positions of the methoxy groups in the benzene ring, when $R_3$=$OCH_3$. If a particular substitution pattern is intended for group B3, it shall be shown as B3($R_2$). Thus, for example, B1($CH_3$, H, 1, Y1, 3, 4) is the 2-(3,4-dimethoxyphenyl)-N-methylethylamino group, B1($C_2H_5$, $CH_3$, 1, Y1, 4) is the N-ethyl-3-(4-methoxyphenyl)-2-propylamino group, and B1($CH_3$, H, 2, Y2, 3, 4) is the 4-cyano-4-(3,4 -dimethoxyphenyl)-5,N-dimethylhexylamino group. Likewise, B3($CH_3$) is the 4-cyano-4-(3,4-dimethoxyphenyl)-N-methylcyclohexylamino group.

X preferably represents one of the X2 or X3 groups; n is preferably an integer from 1 to 3; and B preferably represents the B1 group, especially the B1($CH_3$, H, 2, Y2, 3, 4) group.

As an example of the use of the above abbreviations, Fl—X2—$(CH_2)_3$—B1($CH_3$, H, 2, Y2, 3, 4) represents the compound 8-{3-[4-cyano-4-(3,4-dimethoxyphenyl)-N,5-dimethylhexylamino]propoxycarbonyl}-3-methyl-4-oxo-2-phenyl-4H-1-benzopyran.

DETAILED DESCRIPTION OF THE INVENTION

All patents, patent applications, and literature references cited herein are hereby incorporated by reference in their entirety.

The compounds according to the invention can generally be prepared by condensing the Fl—X—(CH$_2$)$_n$—Hal compounds, where Hal is a halogen atom, preferably a chlorine or bromine atom, with an H-B compound. Condensation is preferably, but not necessarily, carried out in a solvent such as dimethylformamide or methanol, usually in the presence of a base such as potassium carbonate. Such condensations are described in the following Examples 1, 4 and 6 to 20.

An alternative method for the preparation of the compounds of the invention is the condensation of a Fl—X—H compound with a Hal—(CH$_2$)$_n$—B compound, where Hal is as above defined.

This condensation may be carried out under the conditions described in the last preceding paragraph, and is illustrated in Example 2.

In some cases, the compounds of the invention can be prepared by a conversion of other compounds of the invention or by the N-oxidation reactions illustrated in Examples 3 and 5 described below.

Yet other methods will appear to be feasible to those skilled in the art.

Starting Materials

The compounds Fl—X—(CH$_2$)$_n$—Hal and Fl—X—H used in the preparation of the compounds of the invention can themselves be obtained from compounds known in the scientific literature, such as Fl—COOH, Fl—COONa, Fl—COCl and Fl—CHO, by conversions known to those skilled in the art. Several of these conversions are described in detail below.

DETAILED PREPARATION OF INTERMEDIATE PRODUCTS 8-(3-Bromopropoxycarbonyl)-3-methyl-4-oxo-2-phenyl-4H-1-benzopyran (Intermediate I)

30 g of 1,3-dibromopropane was added dropwise at ambient temperature to a suspension of 30 g of sodium 3-methyl-4-oxo-2-phenyl-4H-1-benzopyran-8-carboxylate in 150 ml of dimethylformamide and 35 ml of water. The reaction mixture was stirred at ambient temperature for 5 days. 100 ml of water were added and stirring was continued for another 15 minutes. The precipitate was filtered by suction, washed with water and purified by flash chromatography on silica gel, eluting with chloroform:ethyl acetate 95:5. The collected fractions were evaporated to dryness in vacuo and the residue was recrystallized from ethanol to give 27.7 g of the title compound, melting point 114°–115° C.

The benzopyran carboxylate salt used in the foregoing synthesis was prepared by dissolving the corresponding acid (104 g) in hot methanol (560 ml) and adding an aqueous solution (280 ml) of sodium hydrogen carbonate (31 g). The desired salt was precipitated out of solution following addition of acetone (850 ml) and collected by suction filtration (62 g, m.p. >280° C.). The corresponding acid was prepared as per Da Re, P. et al., *J. Med. Pharm. Chem.* 2: 263, 1960.

8-Hydroxymethyl-3-methyl-4-oxo-2-phenyl-4H-1-benzopyran (Intermediate II)

467 ml of a 1.48N sodium borohydride solution in dimethylformamide was added over a period of 30 minutes, with stirring at ambient temperature, to a solution of 100 g of 3-methyl-4-oxo-2-phenyl-4H-1-benzopyran-8-carbonyl chloride (prepared as described in Da Re, P. et al., *J. Med. Pharm. Chem.* 2: 263 (1960)) in 1 liter of anhydrous dimethylformamide and the reaction mixture was stirred for 2.5 hours at ambient temperature. Maintaining the reaction mixture temperature at 0°–5° C., 88 ml of 2N hydrochloric acid was added to the mixture followed by addition of 102 ml of a 12.7N sodium hydroxide solution. The resultant mixture was poured into 6 liters of water, stirred for 3 hours, and filtered by suction. The solid, sequentially washed with a 4N sodium hydroxide solution and water, was then crystallized from methanol. Yield: 50 g of the title compound, melting point 145°–147° C.

8-Acetyl-3-methyl-4-oxo-2-phenyl-4H-1-benzopyran (Intermediate III)

1.17 g of magnesium turnings, 7.4 ml of anhydrous ethanol and 0.2 ml of anhydrous carbon tetrachloride were placed in a flask under a stream of nitrogen. When the temperature started to rise, 7.5 ml of anhydrous chlorobenzene was added, followed by the slow addition (25 minutes) of a solution of 5.28 ml of anhydrous diethyl malonate and 3.5 ml of anhydrous chlorobenzene in 16 ml of anhydrous ethanol. The reaction flask was heated at 75° C. for two hours, cooled to 25° C., and a solution of 8.8 g of 3-methyl-4-oxo-2-phenyl-4H-1-benzopyran-8-carbonyl chloride in 88 ml of anhydrous chlorobenzene was slowly added, without exceeding 35° C. The reaction mixture was stirred for two more hours at 35° C. and then cooled to 0° C. 13 ml of water and 1.9 ml of sulfuric acid (d=1.84) were added. The resulting solution was decanted from the insoluble inorganic matter and stripped in vacuo.

The crude acylmalonate obtained was refluxed for six hours with 10.4 ml of acetic acid, 7 ml of water and 1.3 ml of sulfuric acid (d=1.84). After cooling, the solution was poured into iced water and the precipitate was collected by suction filtration and washed with aqueous sodium carbonate. Crystallization from 90% ethanol gave 6.5 g of the title compound, melting point 159°–161° C.

8-Bromoacetyl-3-methyl-4-oxo-2-phenyl-4H-1-benzopyran (Intermediate IV)

A solution of 11.2 g of bromine in 250 ml of chloroform was added, over a period of two hours at 20°–25° C., to a solution of 19.5 g of Intermediate III in 700 ml of chloroform. After stirring for 1 hour at 20°–25° C., the solution was washed with 400 ml of an aqueous 2N sodium hydroxide solution and then repeatedly with water, dried with anhydrous sodium sulphate and stripped in vacuo. The crude product was treated with diethyl ether, collected by suction filtration and crystallized from acetone, to give 16 g of the title compound, melting point 134°–135° C.

8-(2-Hydroxyethylcarbamoyl)-3-methyl-4-oxo-2-phenyl-4H-1-benzopyran (Intermediate V)

The title compound was prepared in the same way as Intermediate XX, and with the same yield, using 2-aminoethanol instead of 3-aminopropanol. Melting point 206°–208° C.

8-[-(2-Hydroxyethyl)-N-methylcarbamoyl]-3-methyl-4-oxo-2-phenyl-4H-1-benzopyran (Intermediate VI)

A solution of 1.6 ml of 2-methylaminoethanol in 10 ml of water was added dropwise over a period of 5 minutes to a suspension of 6 g of 3-methyl-4-oxo-2-phenyl-4H-1-benzopyran-8-carbonyl chloride (prepared as described in Da Re, P. et al., *J. Med. Pharm. Chem.* 2: 263 (1960)) and 1.52 g of potassium carbonate in 60 ml of acetone. After stirring for 2.5 hours at 20°–25° C., the solvent was removed in vacuo and the residue was taken up in 150 ml of acetone. The mixture was refluxed for 15 minutes, and was then filtered. The solvent was evaporated from the filtrate and the residue was dissolved in 20 ml of dimethylformamide, treated with 14 ml of a 1.4% sodium carbonate solution, stirred for 30 minutes at 20°–25° C. and diluted by addition of 150 ml of water. The mixture was extracted with chloroform and the organic layer was washed with 0.5N hydrochloric acid and then with water. The solution was dried on anhydrous sodium sulphate, filtered and evaporated to dryness in vacuo. The resulting oil was taken up in 200 ml of diethyl ether and stirred for 2 hours at 20°–25° C. The solid was collected by filtration and crystallized from ethyl acetate to give 2.97 g of the title compound, melting point 128°–130° C.

8-(2-Chloroethylcarbamoyl)-3-methyl-4-oxo-2-phenyl-4H-1-benzopyran (Intermediate VII)

The title compound was prepared in the same way and with comparable yield as Intermediate XXI, using Intermediate V in place of Intermediate XX and carrying out the reaction at ambient temperature. Melting point 181°–182° C. (ethyl acetate).

8-[(2-Chloroethyl)-N-methylcarbamoyl]-3-methyl-4-oxo-2-phenyl-4H-1-benzopyran (Intermediate VIII)

A solution of 1.1 ml of thionyl chloride in 2 ml of dichloromethane was added to a solution of 3.37 g of Intermediate VI in 20 ml of dichloromethane, and the mixture was stirred for 4 hours at ambient temperature. The removal of the solvent in vacuo gave an oil which was taken up in diethyl ether. 3 g of the title compound precipitated as a white solid which was filtered and used with no further purification. Melting point 126°–128° C. (diethyl ether).

8-(2-Chloroethoxymethyl)-3-methyl-4-oxo-2-phenyl-4H-1-benzopyran (Intermediate IX)

6 ml of thionyl chloride in 18 ml of chloroform was added with stirring at 0° C. to a solution of 23 g of Intermediate XIII and 11 ml of triethylamine in 185 ml of chloroform. The reaction mixture was heated to 70° C. and stirred for 2 hours. After cooling to ambient temperature, the mixture was poured into water and the organic layer was separated, washed with a sodium chloride solution, dried on anhydrous sodium sulphate and evaporated to dryness in vacuo to give 24 g of the title compound melting at 102°–103° C. (ethanol).

8-Chloromethyl-3-methyl-4-oxo-2-phenyl-4H-1-benzopyran (Intermediate X)

53.4 g of Intermediate II and 38.8 ml of anhydrous triethylamine were dissolved in 440 ml of chloroform. A solution of 19.8 ml of thionyl chloride in 80 ml of anhydrous chloroform was added to the above solution, which was maintained at −10°/−2° C. The reaction mixture was stirred at ambient temperature for 4 hours, and then diluted with 400 ml of water. The aqueous phase was extracted with chloroform, and the extracts were added to the chloroform phase. The chloroform solution was washed with brine, dried on anhydrous sodium sulphate and evaporated to dryness in vacuo. Yield: 56 g of the title compound, which, recrystallized from ethanol, has a melting point of 112°–113° C.

8-Methylaminomethyl-3-methyl-4-oxo-2-phenyl-4H-1-benzopyran (Intermediate XI)

A solution of 15.1 g of anhydrous zinc chloride and 14.5 g of sodium cyanoborohydride in 400 ml of anhydrous methanol was added dropwise with stirring at 0° C. to a mixture of 58 g of 8-formyl-3-methyl-4-oxo-2-phenyl-4H-1-benzopyran (prepared as described in Uneyama, K. et al., *Bull. Chem. Soc. Jap.* 58:2361 (1985)), 60.7 g of methylamine hydrochloride and 125 ml of triethylamine in 600 ml of anhydrous methanol. After stirring for 5 hours at 20°–25° C., the solvent was evaporated off in vacuo and the residue was taken up in 200 ml of water and collected by suction filtration. The crude product was dissolved in aqueous acetic acid, washed with ethyl acetate and reprecipitated by the addition of a 6N sodium hydroxide solution. 49 g of the title compound was obtained, with a melting point of 97°–99° C., after crystallization from 75% ethanol.

8-(2-Chloroethylthiomethyl)-3-methyl-4-oxo-2-phenyl-4H-1-benzopyran (Intermediate XII)

A solution of 37 g of Intermediate X and 10.5 g of thiourea in 370 ml of ethanol was refluxed for 1 hour. The reaction mixture was cooled to ambient temperature, and 42 g of 8-amidinothiomethyl-3-methyl-4-oxo-2-phenyl-4H-1-benzopyran hydrochloride spontaneously crystallized. A sample recrystallized from ethanol had a melting point of 233°–235° C.

48 ml of a 35% aqueous sodium hydroxide solution are added with vigorous stirring to a suspension of 35 g of the compound prepared as above and 1.05 g of benzyl triethylammonium chloride in 440 ml of 1,2-dichloroethane. The mixture was stirred for 2.5 hours at 20°–25° C. and then poured into 300 ml of water. The aqueous layer was extracted with 1,2-dichloroethane and the extracts were added to the organic layer, which was washed with a sodium chloride solution, dried on anhydrous sodium sulphate and evaporated to dryness in vacuo. The residue was crystallized from ethanol, to give 22 g of the title compound, melting point 82°–83° C.

8-(2-Hydroxyethoxymethyl)-3-methyl-4-oxo-2-phenyl-4H-1-benzopyran (Intermediate XIII)

A solution of 2.5 g of Intermediate X in 25 ml of xylene and 3 ml of dioxane was prepared. 0.15 g of sodium was dissolved in 3.10 ml of anhydrous ethylene glycol, and this solution was added dropwise at ambient temperature to the solution of Intermediate X, and then refluxed for 5.5 hours. The reaction mixture was cooled to ambient temperature, poured into 50 ml of water and extracted with dichloromethane. The extract was washed with a sodium chloride solution, dried on anhydrous sodium sulphate and evaporated to dryness in vacuo. The solid residue was crystallized from ethanol, to give 2.1 g of the title compound, melting point 132°–133° C.

8-Aminomethyl-3-methyl-4-oxo-2-phenyl-4H-1-benzopyran (Intermediate XIV)

A mixture of 21 g of Intermediate XVII and 19 g of triphenylphosphine in 160 ml of tetrahydrofuran was stirred at ambient temperature for 8 hours. A thin layer chromatographic test showed the disappearance of Intermediate XVII. 3 ml of water was added, and stirring was continued for another 24 hours. The solvents were removed in vacuo and the residue was dissolved in water containing a slight excess of acetic acid. The aqueous solution was washed with ethyl acetate, made basic with a 37% sodium hydroxide solution and filtered by suction. The solid was washed with water and dried to give 18 g of the title compound. The hydrochloride, recrystallized from ethanol, had a melting point of 256°–258° C.

8-(2-Chloroethylsulphonylmethyl)-3 -methyl-4-oxo-2-phenyl-4H-1-benzopyran (Intermediate XV)

41.6 ml of 30% hydrogen peroxide was added dropwise at 40° C. over a period of 20 minutes to a solution of 26.2 g of Intermediate XII in 300 ml of glacial acetic acid. The mixture was heated at 60° C. with stirring for 4.5 hours, then cooled to ambient temperature and poured into 60 ml of water. Suction filtration gave a solid which was washed with water and dried, to give 29.4 g of the title compound. Melting point 158°–161° C. (ethanol).

8-[N-Methyl-N-(2-chloroethyl)aminomethyl]-3-methyl-4-oxo-2-phenyl-4H-1-benzopyran (Intermediate XVI)

A mixture of 22 g of Intermediate XI, 66 ml of 1-bromo-2-chloroethane and 11 g of anhydrous potassium carbonate in 88 ml of dimethylformamide was stirred at 20°–251° C. for 12 hours. The reaction mixture was then poured into 600 ml of water and extracted with dichloromethane. The organic layer was washed with water, dried on anhydrous sodium sulphate and acidified with hydrochloric acid in ethanol. The solvent and the excess 1-bromo-2-chloroethane were distilled off in vacuo at 70°–80° C. The residue was taken up in an aqueous 1N sodium hydroxide solution and extracted with dichloromethane. The organic solution was washed with water, dried on anhydrous sodium sulphate and evaporated to dryness in vacuo at 25°–30° C. The crude residue was purified by flash chromatography on silica gel, eluting with ethyl acetate:petroleum ether (7:3), to give 18 g of the title compound. Melting point 118°–120° C. (ethanol).

8-Azidomethyl-3-methyl-4 -oxo-2-phenyl-4H-1-benzopyran (Intermediate XVII)

A mixture of 22.8 g of Intermediate X and 6.8 g of sodium azide in 110 ml of dimethylformamide was stirred for 3 hours at 100° C. After cooling to ambient temperature, 130 ml of water and 88 ml of ethanol were added to the reaction mixture. After 1 hour, the crystals were collected by suction filtration, washed with water and dried. Yield: 22 g of the title product, melting point 132°–134° C. (ethanol).

8-(N-Methyl-N-chloracetylaminomethyl)-3-methyl-4-oxo-2-phenyl-4H-1-benzopyran (Intermediate XVIII)

A solution of 6 ml of chloroacetyl chloride in 60 ml of 1,2-dichloroethane was added dropwise at −5°/0° C. to a solution of 20 g of Intermediate XI and 10 ml of triethylamine in 200 ml of 1,2-dichloroethane. After stirring at 20°–25° C. for 2 hours, 150 ml of water was added to the reaction mixture and the phases were separated. The organic phase was washed with water and dried on anhydrous sodium sulphate. The solvent was removed in vacuo, and the residue was crystallized from ethanol to give 22.5 g of the title compound, melting point 146°–148° C.

8-Chloroacetamidomethyl-3-methyl-4-oxo-2-phenyl-4H-1-benzopyran (Intermediate XIX)

A solution of 3.2 ml of chloroacetyl chloride in 32 ml of 1,2-dichloroethane was added dropwise with stirring at −5° C. to a mixture of 10 g of Intermediate XIV and 5.5 ml of triethylamine in 80 ml of 1,2-dichloroethane. The reaction mixture was stirred at ambient temperature for 1 hour, then 150 ml of water was added. The phases were separated and the aqueous phase was extracted with 1,2-dichloroethane. The extracts were combined with the organic phase and washed with a cold saturated sodium bicarbonate solution and water, then dried on anhydrous sodium sulphate. Solvent was removed in vacuo and the resultant residue was crystallized from ethanol to give 10.7 g of the title compound, melting point 152°–155° C.

8-(3-Hydroxypropylcarbamoyl)-3-methyl-4-oxo-2-phenyl-4H-1-benzopyran (Intermediate XX)

A solution of 7.6 ml of 3-aminopropanol in 50 ml of water was added dropwise over a period of 30 minutes to a suspension of 30 g of 3-methyl-4-oxo-2-phenyl-4H-1-benzopyran-8-carbonyl chloride and 15.2 g of potassium carbonate in 400 ml of acetone. The thick suspension was stirred for 3 hours at 20°–25° C. The solvents were removed in vacuo and the residue was taken up in 300 ml of water. After stirring for 1 hour, the precipitate was collected by suction filtration and washed with water. The crude product was purified by crystallization from 95% ethanol to give 23.8 g of the title compound, melting point 191°–193° C. Another 4.7 g of the title compound was obtained by concentration in vacuo of the crystallization liquors.

8-(3-Chloropropylcarbamoyl)-3-methyl-4-oxo-2-phenyl-4H-1-benzopyran (Intermediate XXI)

A solution of 1.1 ml of thionyl chloride in 2 ml of chloroform was added to a boiling solution of 3.37 g of Intermediate XX in 20 ml of chloroform. After refluxing for 90 minutes, the solvent was removed in vacuo and the residue was crystallized from acetonitrile to give 3 g of the title compound with a melting point of 193°–194° C.

EXAMPLES

Example 1

8-{2-[4-Cyano-4-(3,4-dimethoxyphenyl)-5,N-dimethylhexylamino]-1-oxoethyl}-3 -methyl-4-oxo-2-phenyl-4H-1-benzopyran hydrochloride hydrate Fl—X1—CH$_2$—B1(CH$_3$, H, 2, Y2, 3, 4)

A solution of 7.84 g of 4-cyano-4-(3,4-dimethoxyphenyl)-5,N-dimethylhexylamine hydrochloride (prepared as described in Laguerre, M. et al., *Eur. J. Med. Chem.* 25:351 (1990)), in 20 ml of anhydrous dimethylformamide was added at 0°–5° C. into a stirred suspension of 7.12 g of Intermediate IV and 6.08 g of anhydrous potassium carbonate in 100 ml of dimethylformamide. Stirring was continued at ambient temperature for 2 hours, and the reaction mixture was then poured into iced water. The resulting precipitate was collected by suction filtration and dissolved in methyl acetate. An excess of 6.7N hydrochloric acid in ethanol was then added to the solution, followed by diethyl ether. The precipitate was collected by filtration and recrystallized from ethyl acetate to give 2.7 g of the title compound, melting point 120°–125° C.

Example 2

8-{3-[2-(3,4-Dimethoxyphenyl)-N-methylethylamino]propoxycarbonyl}-3-methyl-4-oxo-2-phenyl-4H-1-benzopyran hydrochloride
Fl—X2—(CH$_2$)$_3$—B1(CH$_3$, H, 1, Y1, 3, 4)

A mixture of 8.4 g of 8-carboxy-3-methyl-4-oxo-2-phenyl-4H-1-benzopyran and 8.28 g of anhydrous potassium carbonate in 120 ml of dimethylformamide is stirred at 80°–85° C. for 30 minutes. After cooling to ambient temperature, 9.78 g of N-(3-chloropropyl)-2-(3,4-dimethoxyphenyl)-N-methylethyl-amine hydrochloride (prepared as described in GB Patent No. 1,290,625) was added. The mixture was stirred for 3.5 hours at 80°–851° C. and then poured into 480 ml of water. The mixture was extracted with diethyl ether and the organic layer was separated, washed with water and dried on anhydrous sodium sulphate. The solvent was evaporated off in vacuo and the oily residue was dissolved in ethanol and acidified by the addition of 5N hydrochloric acid in isopropanol. The title compound was collected by filtration and crystallized from methanol. Yield 12.58 g, melting point 225°–226° C.

Example 3

8-{3-[2-(3,4-Dimethoxyphenyl)-N-methyl-N-oxoethylamino]-propoxycarbonyl}-3-methyl-4-oxo-2-phenyl-4H-1-benzopyran hydrochloride
N-oxide of Fl—X2—(CH$_2$)$_3$—B1(CH$_3$, H, 1, Y1, 3, 4)

A solution of 2.1 g of m-chloroperbenzoic acid in 200 ml of dichloromethane was added dropwise over a period of 2 hours at 0°–5° C. to a solution of 5.67 g of the compound prepared in Example 2 in 132 ml of dichloromethane. The mixture was then stirred for an additional 2 hours at 0°–5° C. and stood overnight at the same temperature. It was then concentrated to 40–45 ml by evaporation in vacuo, and acidified with a solution of 3.5N hydrochloric acid in diethyl ether. The salt was precipitated by addition of diethyl ether and the pasty crude product was taken up in acetone and crushed. The solid was collected by filtration and crystallized from ethanol, to give 5.72 g of the title compound melting at 142°–144° C.

Example 4

8-{3-[4-Cyano-4-(3,4-dimethoxyphenyl)-N,5-dimethylhexylamino]propoxycarbonyl}-3-methyl-4-oxo-2-phenyl-4H-1-benzopyran hydrochloride Fl—X2—(CH$_2$)$_3$—B1(CH$_3$, H, 2, Y2, 3, 4)

A mixture of 12 g of Intermediate I, 8.6 g of 4-cyano-4-(3,4-dimethoxyphenyl)-5,N-dimethylhexylamine and 6.2 g of anhydrous potassium carbonate in 30 ml of anhydrous dimethylformamide was stirred at ambient temperature for 2 days. After pouring into cold water, the mother liquors was decanted and the pasty precipitate was dissolved in diethyl ether. The organic solution was washed with water to neutrality and dried on anhydrous sodium sulphate. The solvent was evaporated off in vacuo and the oily residue was purified by flash chromatography on silica gel, eluting with chloroform:methanol 98:2. The fractions containing the pure base of the title compound were pooled, the solvents removed in vacuo and the residue was dissolved in isopropanol and acidified with 5N hydrochloric acid in isopropanol. The salt, collected by suction filtration, was recrystallized from isopropanol to give 9.72 g of the title compound, melting at 146°–150° C.

Example 5

8-{3-[4-Cyano-4-(3,4-dimethoxyphenyl)-N,5-dimethyl-N-oxohexylamino]propoxycarbonyl}-3-methyl-4-oxo-2-phenyl-4H-1-benzopyran hydrochloride x 0.25 H$_2$O N-oxide of
Fl—X2—(CH$_2$)$_3$—B1(CH$_3$, H, 2, Y2, 3, 4)

This compound was prepared according to the method of Example 3, starting from the compound prepared in Example 4 instead of that prepared in Example 2. The salt was collected by filtration and crystallized from methanol-diethyl ether (2:5). Melting point 148°–151° C.

Example 6

8-{3-[N-Ethyl-3-(4-methoxyphenyl)-2-propylamino]propoxycarbonyl}-3-methyl-4-oxo-2-phenyl-4H-1-benzopyran hydrochloride
Fl—X2—(CH$_2$)$_3$—B1(C$_2$H$_5$, CH$_3$, 1, Y1, 4)

This compound was prepared by the method of Example 4, using N-ethyl-3-(4-methoxyphenyl)-2-propylamine (prepared as described in Fusco, R. et al., *Il Farmaco* 3:125 (1948)) in place of 4-cyano-4-(3,4-dimethoxyphenyl)-5,N-dimethylhexylamine. The reaction was carried out for 24 hours at ambient temperature and then 12 hours at 85°–90° C. The title compound containing 2.24% of water was obtained, melting point 152°–155° C. (isopropanol), yield 30%.

Example 7

8-{3-[1-(3,4-Dimethoxybenzyl)-6,7-dimethoxy-2H-1,2,3,4-tetrahydro-2-isoquinolinyl]propoxycarbonyl}-3-methyl-4-oxo-2-phenyl-4H-1-benzopyran hydrochloride Fl—X2—(CH$_2$)$_3$—B2

This compound was prepared by the method of Example 4, using 1-(3,4-dimethoxybenzyl)-6,7-dimethoxy-2H-1,2,3,4-tetrahydroisoquinoline (prepared as described in Stenlake, J. B. et al., *Eur. J. Med. Chem.* 9:233 (1974)) instead of 4-cyano-4-(3,4-dimethoxyphenyl)-5,N-dimethylhexylamine. The reaction was carried out for 2 hours at ambient temperature and then 6 hours at 60° C. The crude base was purified by chromatography on silica gel using ethyl acetate-chloroform (4:1) as eluant. The salt was made in methanol:acetone (4:1) by addition of 3N hydrochloric acid in methanol. Melting point 220°–222° C. (80% ethanol), yield 58%. The title compound contained 1.83% of water.

Example 8

8-<3-{3-[2-(3,4-Dimethoxyphenyl)-1,1,3,3-tetraoxo-1,3-dithian-2-yl]-N-methylpropylamino}propoxycarbonyl>-3-methyl-4-oxo-2-phenyl-4H-1-benzopyran hydrochloride
Fl—X2—(CH$_2$)$_3$—B1(CH$_3$, H, 2, Y3, 3, 4)

This compound was prepared by the method of Example 4, using 3-[2-(3,4-dimethoxyphenyl)-1,1,3,3-tetraoxo-1,3-dithian-2-yl]-N-methylpropylamine (prepared as described in Ramuz, H., Arzneim.-Forsh. 28:2051 (1978)) instead of 4-cyano-4-(3,4-dimethoxyphenyl)-5,N-dimethylhexylamine. The reaction was carried out for 12 hours at 60° C.

The crude base was purified by flash chromatography on silica gel, using ethyl acetate:methanol as an eluant and graduating it from 7:3 to 1:1. The hydrochloride was isolated in amorphous form and contained 1.1% ethyl acetate. Melting point 140°–145° C. with decomposition.

Example 9

(Z)-8-{3-[4-Cyano-4-(3,4-dimethoxyphenyl)-N-methylcyclohexylamino]propoxycarbonyl}-3-methyl-4-oxo-2-phenyl-4H-1-benzopyran methanesulphonate
Cis—Fl—X2—(CH$_2$)$_3$—B3(CH$_3$)

This compound was prepared by the method of Example 4, using (Z)-4-cyano-4-(3,4-dimethoxyphenyl)-N-methylcyclohexylamine (prepared as described in Dei, S. et al., *J. Med. Chem.* 34:2219 (1991)) instead of 4-cyano-4-(3,4-dimethoxyphenyl)-5,N-dimethylhexylamine. The reaction was carried out at ambient temperature for 5 days. The crude base was purified by flash chromatography on silica gel, eluting with ethyl acetate-methanol (9:1). The fractions containing the base of the title compound were pooled, the solvents removed in vacuo and the residue was dissolved in dichloromethane. The solution was acidified with methanesulphonic acid. The salt, precipitated by the addition of diethyl ether, was collected by filtration. Melting point 204°–206° C. (ethanol).

Example 10

(E)-8-{3-[4-Cyano-4-(3,4-dimethoxyphenyl)-N-methylcyclohexylamino]propoxycarbonyl}-3-methyl-4-oxo-2-phenyl-4H-1-benzopyran methanesulphonate
Trans—Fl—X2—(CH$_2$)$_3$—B3(CH$_3$)

This compound was prepared by the method of Example 9, using (E)-4-cyano-4-(3,4-dimethoxyphenyl)-N-methylcyclohexylamine (prepared as described in Dei, S. et al., *J. Med. Chem.* 34:2219 (1991)) instead of the Z isomer. The reaction was carried out for 7 days. Melting point 194°–196° C. (methylene chloride-ethyl acetate).

Example 11

8-{3-[4-Cyano-4-(3,4-dimethoxyphenyl)-N,5-dimethylhexylamino]propylcarbamoyl}-3-methyl-4-oxo-2- phenyl-4H-1-benzopyran hydrochloride hemihydrate
Fl—X3—(CH$_2$)$_3$—B1(CH$_3$, H, 2, Y2, 3, 4)

A mixture of 5.8 g of 4-cyano-4-(3,4-dimethoxyphenyl)-N,5-dimethylhexylamine and 3.56 g of Intermediate XXI was heated at 180° C. for 2 hours. After cooling, the dark mass was purified by flash chromatography on silica gel, eluting with dichloromethane-methanol (100:3). The fractions containing the base of the title compound were pooled and evaporated to dryness in vacuo. The residue was dissolved in boiling ethanol, filtered and acidified with 5N hydrochloric acid in ethanol. The solvent was evaporated off in vacuo, the residue was taken up in diethyl ether and the suspension was stirred for 5 hours. The amorphous salt was collected by filtration and dried at 50° C./0.2 mmHg for 30 hours to give 5.3 g of the title compound, melting point 95°–125° C.

| Elemental Analysis for C$_{37}$H$_{43}$N$_3$O$_5$.HCl.0.5H$_2$O | | | | | | | | | | | | |
|---|---|---|---|---|---|---|---|---|---|---|---|---|
| calculated: | C | 67.82 | H | 6.92 | N | 6.41 | Cl | 5.41 | H$_2$O | 1.37 |
| found: | | 67.44 | | 6.98 | | 6.36 | | 5.41 | | 1.33 |

Example 12

8-{3-[2-(3,4-Dimethoxyphenyl)-N-methylethylamino]propylcarbamoyl}-3-methyl-4-oxo-2-phenyl-4H -1-benzopyran hydrochloride 0.3-hydrate Fl—X3—(CH$_2$)$_3$—B1(CH$_3$, H, 1, Y1, 3, 4)

This compound was prepared according to the method described in Example 11, using 2-(3,4-dimethoxyphenyl)-N-methylethylamine (prepared as described in Nelson, W. L. et al., *J. Org. Chem.* 52:1309 (1987)) instead of 4-cyano-4-(3,4-dimethoxyphenyl)-5,N-dimethylhexylamine. The reaction was carried out for 5 hours and the crude base obtained by chromatographic purification was crystallized from ethanol. The hydrochloride was prepared from the crystallized base, melting point 195°–197° C.

Example 13

8-{2-[4-Cyano-4-(3,4-dimethoxyphenyl)-N,5-dimethylhexylamino]ethylcarbamoyl}-3 -methyl-4-oxo-2-phenyl-4H-1-benzopyran hydrochloride hemihydrate
Fl—X3—(CH$_2$)$_2$—B1(CH$_3$, H, 2, Y2, 3, 4)

A mixture of 3.41 g of Intermediate VII, 2.9 g of 4-cyano-4-(3,4-dimethoxyphenyl)-5,N-dimethylhexylamine, 2.75 g of anhydrous potassium carbonate and 1.66 g of potassium iodide in 30 ml of anhydrous dimethylformamide was stirred at 55°–60° C. for 30 hours and then at 70°–80° C. for 12 hours. The solvent was evaporated off in vacuo, and the residue was taken up in water and extracted with chloroform. The organic layer was separated from the aqueous layer, washed with water and dried on anhydrous sodium sulphate. The solvent was evaporated off in vacuo and the residue was purified by flash chromatography on silica gel, eluting with dichloromethane-methanol (100:2). The fractions containing the title compound as a base were pooled and evaporated to dryness in vacuo. The residue was dissolved in ethanol and the resulting solution was filtered and acidified with 5N hydrochloric acid in ethanol. The solvent was evaporated off and the residue dried at 78° C./0.5 mmHg for 8 hours to give 2.3 g of the title compound, melting point 101°–103° C.

Example 14

8-{2-[4-Cyano-4-(3,4-dimethoxyphenyl)-N,5-dimethylhexylamino]-N-methylethylcarbamoyl}-3-methyl-4-oxo-2-phenyl-4H-1-benzopyran hydrochloride hydrate Fl—X4—(CH$_2$)$_2$—B1(CH$_3$, H, 2, Y2, 3, 4)

This compound was prepared according to the method described in Example 13, using Intermediate VIII instead of Intermediate VII. The reaction was carried out at 100° C. for 6 hours and the hydrochloride was prepared in anhydrous ethanol. The title compound was dried at ambient temperature at 0.5 mmHg for 16 hours. Melting point 102°–106° C.

Example 15

8-{2-[4-Cyano-4-(3,4-dimethoxyphenyl)-N,5-dimethylhexylamino]-N-methylethylaminomethyl}-3-methyl-4-oxo-2-phenyl-4H-1-benzopyran hydrochloride hydrate Fl—X6—(CH$_2$)$_2$—B1(CH$_3$, H, 2, Y2, 3, 4)

A mixture of 4.5 g of Intermediate XVI, 7.68 g of 4-cyano-4-(3,4-dimethoxyphenyl)-5,N-dimethylhexylamine and 1.23 g of potassium iodide in 100 ml of anhydrous dimethylformamide was stirred at 80° C. for 5.5 hours. The mixture was cooled to ambient temperature, poured into water and extracted with ethyl acetate. The combined extracts were washed with brine, dried on anhydrous sodium sulphate and evaporated to dryness in vacuo. The residue was purified by flash chromatography on silica gel, eluting with ethyl acetate-methanol (9:1). The collected fractions containing the title compound as a base, were evaporated to dryness in vacuo. The residue was dissolved in ethanol and 1 molar equivalent of 1N hydrochloric acid in ethanol was added. The ethanol was evaporated off in vacuo and the residue was stirred in isopropyl ether and then filtered. Yield 3.5 g of the title compound melting at 105° C.

Example 16

8-{2-[4-Cyano-4-(3,4-dimethoxyphenyl)-N,5-dimethylhexylamino]-1-oxoethylaminomethyl}-3-methyl-4-oxo-2-phenyl-4H-1-benzopyran hydrochloride dihydrate Fl—X7—CH$_2$—B1(CH$_3$, H, 2, Y2, 3, 4)

A mixture of 3.5 g of Intermediate XIX, 3.64 g of 4-cyano-4-(3,4-dimethoxyphenyl)-5,N-dimethylhexylamine hydrochloride and 3.57 g of anhydrous potassium carbonate in 14 ml of anhydrous dimethylformamide was stirred at ambient temperature for 24 hours. The reaction mixture was poured into water and extracted with dichloromethane. The organic layer was washed with brine, dried on anhydrous sodium sulphate and evaporated to dryness in vacuo. The residue was crystallized from acetone to give the title compound as a base, which was dissolved in ethyl acetate and treated with excess of 5N hydrochloric acid in ethanol. The solid was collected by filtration and recrystallized from ethanol to give 2.45 g of the title compound with a melting point of 139°–142° C.

Example 17

8-{2-[4-Cyano-4-(3,4-dimethoxyphenyl)-N,5-dimethylhexylamino]-N-methyl-1-oxo-ethylaminomethyl}-3-methyl-4-oxo-2-phenyl-4H-1-benzopyran hydrochloride hydrate Fl—X8—CH$_2$—B1(CH$_3$, H, 2, Y2, 3, 4)

A mixture of 4 g of Intermediate XVIII, 3.4 g of 4-cyano-4-(3,4-dimethoxyphenyl)-5,N-dimethylhexylamine and 1.6 g of anhydrous potassium carbonate was stirred at ambient temperature for 3 hours. The reaction mixture was then diluted with water and extracted with dichloromethane. After washing with brine and drying over anhydrous sodium sulphate, the organic layer was evaporated to dryness in vacuo. The resultant crude oily residue was purified by flash chromatography on silica gel, eluting with ethyl acetate-petroleum ether (8:2). Fractions containing the title compound as a base were pooled and evaporated to dryness in vacuo and the residue was dissolved in ethyl acetate. The solution was acidified with a 3N solution of hydrochloric acid in diethyl ether to give, after recrystallization from acetone, 3.25 g of the title compound, melting at 94°–125° C. with decomposition.

Example 18

8-{2-[4-Cyano-4-(3,4-dimethoxyphenyl)-5,N-dimethylhexylamino]ethoxymethyl}-3-methyl-4-oxo-2-phenyl-4H-1-benzopyran hydrochloride hydrate Fl—X9—(CH$_2$)$_2$—B1(CH$_3$, H, 2, Y2, 3, 4)

A mixture of 3.6 g of Intermediate IX, 3.2 g of 4-cyano-4-(3,4-dimethoxyphenyl)-5,N-dimethylhexylamine, 1.73 g of potassium iodide and 1.5 g of anhydrous potassium carbonate in 50 ml of anhydrous dimethylformamide was stirred at 95° C. for 2 hours. The reaction mixture was cooled to ambient temperature, poured into water and extracted with ethyl acetate. The extracts collected were washed with a saturated sodium thiosulfate solution and brine, then dried over anhydrous sodium sulphate. The solution was evaporated to dryness in vacuo, and the oily residue was purified by flash chromatography on silica gel, eluting with ethyl acetate-methanol (97:3). The collected fractions were evaporated to dryness in vacuo and dissolved in diethyl ether. An excess of a 3N hydrochloric acid solution in diethyl ether was added. The solvent was removed, and the residue crystallized from ethyl acetate to give 3.3 g of the title compound melting at 117°–120° C.

Example 19

8-{2-[4-Cyano-4-(3,4-dimethoxyphenyl)-5,N-dimethylhexylamino]ethylthiomethyl}-3-methyl-4-oxo-2-phenyl-4H-1-benzopyran hydrochloride Fl—X10—(CH$_2$)$_2$—B1(CH$_3$, H, 2, Y2, 3, 4)

A mixture of 3.8 g of Intermediate XII, 3.5 g of 4-cyano-4-(3,4-dimethoxyphenyl)-5,N-dimethylhexylamine, 1.63 g of potassium carbonate and 1.92 g of potassium iodide in 38 ml of anhydrous dimethylformamide was stirred at 90° C. for 2 hours. After cooling to ambient temperature, the reaction mixture was poured into water and extracted with ethyl acetate. The organic layer was washed with a saturated sodium thiosulfate solution and then with brine and was finally dried over anhydrous sodium sulphate. The solvent was evaporated off in vacuo to give an oily residue which was purified by flash chromatography on silica gel, eluting with ethyl acetate-petroleum ether 8:2. The fractions containing the title compound as a base were collected and evaporated to dryness in vacuo. The residue was dissolved in diethyl ether and treated with a 3N solution of hydrochloric acid in diethyl ether to give, after filtration, 4.85 g of the title compound, melting at 110°–115° C.

Example 20

8-{2-[4-Cyano-4-(3,4-dimethoxyphenyl)-5,N-dimethylhexylamino]ethylsulphonylmethyl}-3-methyl-4-oxo-2-phenyl-4H-1-benzopyran hydrochloride hemihydrate Fl—X12—(CH$_2$)$_2$—B1(CH$_3$, H, 2, Y2, 3, 4)

A mixture of 3.9 g of Intermediate XV, 3.24 g of 4-cyano-4-(3,4-dimethoxyphenyl)-5,N-dimethylhexylamine and 0.73 g of anhydrous potassium carbonate in 40 ml of anhydrous dimethylformamide was stirred at ambient temperature for 3 hours. The reaction mixture was poured into water and filtered. The solid was washed with water, dried and purified by flash chromatography on silica gel, eluting with petroleum ether-ethyl acetate 4:3, to give the title compound as a base. A solution of the base in acetone was treated with a 3N hydrochloric acid solution in diethyl ether. The solvents were evaporated off and the residue was stirred in diethyl ether to give 3.8 g of the title compound with a melting point of 206° C.

Example 21

The following ingredients are thoroughly mixed and pressed into single tablets:

| Ingredients | Quantity per tablet, mgs. |
| --- | --- |
| Compound Ex. No. 4 | 25 |
| Cornstarch | 20 |
| Lactose | 154 |
| Magnesium stearate | 1 |

Example 22

The following ingredients are thoroughly mixed and pressed into single scored tablets:

| Ingredients | Quantity per tablet, mgs. |
| --- | --- |
| Compound Ex. No. 4 | 100 |
| Lactose | 25 |
| Microcrystalline cellulose | 74 |
| Magnesium stearate | 1 |

Example 23

The following ingredients are mixed and introduced into a hard-shell gelatin capsule:

| Ingredients | Quantity per tablet, mgs. |
| --- | --- |
| Compound Ex. No. 11 | 50 |
| Cornstarch | 19 |
| Lactose | 40 |
| Magnesium stearate | 1 |

Example 24

As injectable preparation buffered to a pH of 7 is prepared having the following composition:

| Ingredients | |
| --- | --- |
| Compound Ex. No. 4 | 0.2 g |
| $K_2HPO_4$ buffer sol. (0.4M) | 2 ml |
| KOH (1 N) | q.s. to pH 7 |
| Distilled sterile water | q.s. to 200 ml |

Example 25

A suppository totaling 2 grams is prepared having the following composition.

| Ingredients | |
| --- | --- |
| Compound Ex. No. 13 | 25 mg |
| Witepsol H-15(*) | balance to 2 g |

(*)Witepsol H-15 is a mixture of triglycerides of saturated vegetable fatty acids produced by Dynamit-Nobel (Germany).

Example 26

An oral suspension is prepared having the following composition:

| Ingredients | |
| --- | --- |
| Compound Ex. No. 17 | 0.1 g |
| Fumaric acid | 0.1 g |
| Sodium chloride | 2.0 g |
| Methyl paraben | 0.1 g |
| Granulated sugar | 25.5 g |
| Sorbitol (70% sol.) | 12.8 g |
| Veegum K (Vanderbilt Co.) | 1.0 g |
| Flavoring | 0.1 ml |
| Distilled water | q.s. to 100 ml |

Example 27

One liter of solution suitable for nasal administration is prepared according to the following composition:

| Ingredients | |
| --- | --- |
| Compound Ex. No. 4 | 50 g |
| EDTA disodium | 0.1 g |
| Nipagin | 0.1 g |
| Distilled water | q.s. to 1 l |

PHARMACOLOGICAL TESTS

Methods

Female Albino Swiss mice [Crl: CD-1 (ICR) BR] with a body weight of 20–30 g and male Sprague Dawley rats [Crl: CD° BR] with a body weight of 200–300 g, from the Charles River Farm, Italy, were used for the trials. The animals were housed with free access to food and water and kept on a forced light-darkness cycle at 22°–24° C. until the day of the trials.

Acute toxicity:

The acute toxicity was evaluated in female Albino Swiss mice after intraperitoneal or oral administrations. Four logarithmic scaled doses of the compounds were dissolved or suspended in 0.5% aqueous Methocel and administered at a volume of 10 ml/kg to groups of 4 mice/dose. The death rate was recorded 7 days after the administration.

Data analysis:

The $LD_{50}$ values and the relevant confidence limits were calculated according to the method of Weil (*Biometrics*, 8, 249, 1952).

Inhibition of $K^+$-induced rat bladder contractions

Male rats were killed by a blow on their heads and their lower abdomens were opened along the midlines. Their urinary bladders were removed by a transverse dissection above the trigone and cut into two fragments (20–30 mm long, 1–2 mm wide). Each fragment was suspended in an isolated organ bath containing 10 ml of a normal Tyrode solution (composition in mM: NaCl 137, KCl 2.68, MgCl$_2$ 1.11, CaCl$_2$ 1.8, NaH$_2$PO$_4$ 0.41, NaHCO$_3$ 11.9, glucose 5.55) and connected, under a steady 1 g load, to an isometric transducer (DY-1, Basile). The solution was gassed with a mixture of 95% O$_2$ and 5% CO$_2$ and heated at 37° C. After a 60 minute equilibration the tension responses to a single KCl dose (Bath concentration=80 mM) inducing phasic and tonic contractions were measured under isometric conditions at 30 minute intervals. After recording one or more reproducible responses, a solution of the test drug was added to the bath (final concentration from $10^{-4}$ to $10^{-9}$M) and 30 minutes later a new contraction was induced.

Data analysis:

The experimental groups were made up of at least 2 preparations from different animals for each drug concentration tested.

The IC$_{50}$ values of the inhibition of the agonist-induced contractions were evaluated by linear regression analysis.

Stability:

The stability at 37° C. and physiological pH (phosphate buffer, pH=7.4) of the ester derivatives, Fl—X2—(CH$_2$)$_n$—B, was evaluated by chromatographic determination of the 3-methyl-4-oxo-2-phenyl-4H-1-benzopyran-8-carboxylic acid resulting from any hydrolysis of the ester group. The stability of the other compounds of the invention was not investigated as they are known to be less subject to degradation than the esters.

Results

The compounds prepared in the Examples were tested according to the above methods, and the results are shown in the following Table, together with comparative results obtained with Flavoxate. The data in the Table confirm that all of the tested compounds, with the exception of Ex. 1 compound, proved to be much more potent than Flavoxate in inhibiting the K+-induced contractions of rat bladder, supporting a better spasmolytic effect for the claimed compounds. In addition, the compounds exhibited lower acute toxicity, with respect to Flavoxate. Also compounds apparently more toxic than Flavoxate (e.g., Ex. 11 and 14 compounds) were considerably safer than Flavoxate because their relative therapeutic index (LD$_{50}$/IC$_{50}$) is higher. Finally, the tested esters proved to be much more stable than Flavoxate at physiological pH. Based on the results shown in the Table, the N-oxide compounds (Example 3 and 5) do not appear to be very active, however they may be useful as prodrugs of more active compounds (see for instance, J. P. Gorrod et al., *Xenobiotica* 341, 1973; M. Strolin Benedetti, *Actual. Chim. Ther.* 18th Series, p. 243, 1991).

TABLE

| Compound Example No. | Inhibition of K+-induced rat bladder contractions IC$_{50}$ (μM) | | Mice LD$_{50}$ (mg/kg) | | Stability at pH 7.4 % Unchanged after 3 h |
|---|---|---|---|---|---|
| | Phasic | Tonic | i.p. | p.o. | |
| 1 | 10.0 | >10.0 | 475 | >3000 | |
| 2 | 1.0 | 0.5 | 773 | 2255 | |
| 3 | >10.0 | >10.0 | >1000 | >3000 | |
| 4 | 0.5 | 1.3 | >1000 | >3000 | 100 |
| 5 | 10.0 | 2.2 | >1000 | >3000 | |
| 6 | 1.7 | 4.2 | >1000 | >3000 | 99 |
| 7 | 1.4 | 0.9 | >1000 | >3000 | 99 |
| 11 | 0.6 | 0.5 | 224 | 400 | |
| 12 | 2.2 | 1.4 | 129 | 716 | |
| 13 | 0.3 | 0.1 | 422 | | |

TABLE-continued

| Compound Example No. | Inhibition of K+-induced rat bladder contractions IC$_{50}$ (μM) | | Mice LD$_{50}$ (mg/kg) | | Stability at pH 7.4 % Unchanged after 3 h |
|---|---|---|---|---|---|
| | Phasic | Tonic | i.p. | p.o. | |
| 14 | 0.1 | 0.1 | 159 | 346 | |
| 16 | 0.5 | 0.9 | 440 | 1280 | |
| 17 | 0.2 | 0.4 | 334 | 1714 | |
| 18 | 0.3 | 0.4 | 334 | 974 | |
| 19 | 0.5 | 1.3 | >1000 | >3000 | |
| 20 | 0.5 | 0.5 | >1000 | >3000 | |
| Flavox. | 13.0 | 13.0 | 385 | 808 | 10 |

What is claimed is:

1. A compound having the general formula I

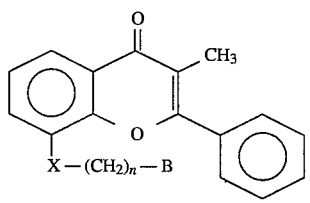

(I)

wherein

X represents one of the following groups, which are shown with the left end as the end linked to the benzopyran ring and the right end as the end linked to the alkylene chain:

(X1) —CO—, (X2) —COO—, (X3) —CONH—, (X4) —CON(CH$_3$)—, (X5) —CH$_2$NH—, (X6) —CH$_2$N(CH$_3$)—, (X7) —CH$_2$NHCO—, (X8) —CH$_2$N(CH$_3$)CO—, (X9) —CH$_2$O—, (X10) —CH$_2$S—, (X11) —CH$_2$SO—, and (X12) —CH$_2$SO$_2$—;

n represents an integer from 1 to 4; and

B represents one of the following groups:

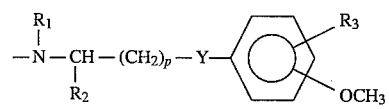

(B1)

wherein R$_1$ represents a lower alkyl (C$_1$–C$_4$) group; R$_2$ represents a hydrogen atom or a lower alkyl (C$_1$–C$_4$) group; R$_3$ represents a hydrogen atom or OR$_4$ group wherein R$_4$ represents a lower alkyl (C$_1$–C$_4$) group; p represents an integer from 1 to 3; and Y represents a valence bond (Y1), or one of the following groups:

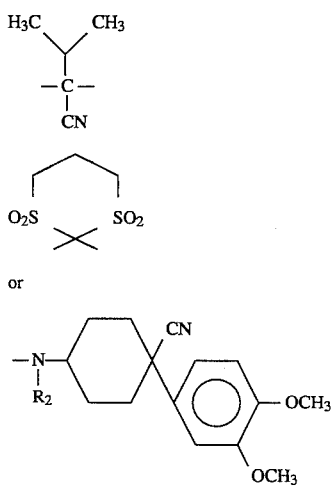

wherein R₂ is as defined above, or an enantiomer, a diastereomer, an N-oxide, a prodrug, a metabolite, or a pharmaceutically acceptable salt of said compound.

2. The compound according to claim 1, wherein X represents one of the groups X2 or X3.

3. The compound according to claim 1, wherein n represents an integer from 1 to 3.

4. The compound according to claim 1, wherein B represents group B1.

5. The compound according to claim 4, wherein B represents a 4-cyano-4-(3,4-dimethoxyphenyl)-N,5-dimethylhexylamino group.

6. A compound selected from the group consisting of:

8-{2-[4-cyano-4-(3,4-dimethoxyphenyl)-5,N-dimethylhexylamino]-1-oxoethyl}-3-methyl-4-oxo-2-phenyl-4H-1-benzopyran, 8-{3-[2-(3,4-dimethoxyphenyl)-N-methylethylamino] propoxycarbonyl}-3-methyl-4-oxo-2-phenyl-4H-1-benzopyran, 8-{3-[2-(3,4-dimethoxyphenyl)-N-methyl-N-oxoethylamino]-propoxycarbonyl}-3-methyl-4-oxo-2-phenyl-4H-1-benzopyran, 8-{3-[4-cyano-4-(3,4-dimethoxyphenyl)-N,5-dimethylhexylamino]propoxycarbonyl}-3-methyl-4-oxo-2-phenyl-4H-1-benzopyran, 8-{3-[4-cyano-4-(3,4-dimethoxyphenyl)-N,5-dimethyl-N-oxohexylamino]propoxycarbonyl}-3-methyl-4-oxo-2-phenyl-4H-1-benzopyran, 8-{3-[N-ethyl-3-(4-methoxyphenyl)-2-propylamino] propoxycarbonyl}-3-methyl-4-oxo-2-phenyl-4H -1-benzopyran, 8-(3-{3-[2-(3,4-dimethoxyphenyl)-1,1,3,3-tetraoxo-1,3-dithian-2-yl]-N-methylpropylamino}propoxycarbonyl)-3-methyl-4-oxo-2-phenyl-4H-1-benzopyran, (Z)-8-{3-[4-cyano-4-(3,4-dimethoxyphenyl)-N-methylcyclohexylamino] propoxycarbonyl}-3-methyl-4-oxo-2-phenyl-4H-1-benzopyran, (E)-8-{3-[4-cyano-4-(3,4-dimethoxyphenyl)-N-methylcyclohexylamino] propoxycarbonyl}-3-methyl-4-oxo-2-phenyl-4H-1-benzopyran, 8-{3-[4-cyano-4-(3,4-dimethoxyphenyl)-N,5-dimethylhexylamino] propylcarbamoyl}-3-methyl-4-oxo-2-phenyl-4H-1-benzopyran, 8-{3-[2-(3,4-dimethoxyphenyl)-N-methylethylamino] propylcarbamoyl}-3-methyl-4-oxo-2-phenyl-4H -1-benzopyran, 8-{2-[4-cyano-4-(3,4-dimethoxyphenyl)-N,5-dimethylhexylamino] ethylcarbamoyl}-3-methyl-4-oxo-2-phenyl-4H -1-benzopyran, 8-{2-[4-cyano-4-(3,4-dimethoxyphenyl)-N,5-dimethylhexylamino] -N-methylethylcarbamoyl}-3-methyl-4-oxo-2-phenyl-4H-1-benzopyran, 8-{2-[4-cyano-4-(3,4-dimethoxyphenyl)-N,5-dimethylhexylamino] -N-methylethylaminomethyl}-3-methyl-4-oxo-2-phenyl-4H-1-benzopyran, 8-{2-[4-cyano-4-(3,4-dimethoxyphenyl)-N,5-dimethylhexylamino] -1-oxoethylaminomethyl}-3-methyl-4-oxo-2-phenyl-4H-1-benzopyran, 8-{2-[4-cyano-4-(3,4-dimethoxyphenyl)-N,5-dimethylhexylamino] -N-methyl-1-oxoethylaminomethyl}-3-methyl-4-oxo-2-phenyl-4H-1-benzopyran, 8-{2-[4-cyano-4-(3,4-dimethoxyphenyl)-5,N-dimethylhexylamino] ethoxymethyl}-3-methyl-4-oxo-2-phenyl-4H-1-benzopyran, 8-{2-[4-cyano-4-(3,4-dimethoxyphenyl)-5,N-dimethylhexylamino] ethylthiomethyl}-3-methyl-4-oxo-2-phenyl-4H-1-benzopyran, and 8-{2-[4-cyano-4-(3,4-dimethoxyphenyl)-5,N-dimethylhexylamino] ethylsulphonylmethyl}-3-methyl-4-oxo-2-phenyl-4H-1-benzopyran.

7. A pharmaceutical composition comprising the compound of claim 1 or pharmaceutically acceptable salt thereof and a pharmaceutically acceptable diluent or carrier.

8. A pharmaceutical composition comprising the compound of claim 6 or an enantiomer, a diastereomer, an N-oxide, a metabolite, or a pharmaceutically acceptable salt of said compound and a pharmaceutically acceptable diluent or carrier.

9. A method for treating bladder contractions in a mammal comprising administering to said mammal a therapeutic effective amount of a compound of claim 1.

10. A method for treating bladder contractions in a mammal comprising administering to said mammal a therapeutic effective amount of a compound of claim 6.

* * * * *

UNITED STATES PATENT AND TRADEMARK OFFICE
CERTIFICATE OF CORRECTION

PATENT NO. : 5,453,518          Page 1 of 2
DATED : September 26, 1995
INVENTOR(S) : Amedeo LEONARDI, Gianni MOTTA, Carlo RIVA and Luciano GUARNERI It is certified that error appears in the above-indentified patent and that said Letters Patent is hereby corrected as shown below:

Abstract, following "and B represents one of the following groups:" insert new line —(B1)—.
Column 4, line 20, change "The    3" to --The 3--".

Column 9, line 25, change "251°" to --25°--.

Column 11, line 15, change "851°" to --85°--;

Column 12, line 46, change "(3,4    -dimethoxyphenyl)" to --(3,4-dimethoxyphenyl)--;
        line 65, change "Arzneim.-Forsh." to --*Arzneim.-Forsh.*--;
        line 66, change "(3,4    -dimethoxyphenyl)" to --(3,4-dimethoxyphenyl)--.

Column 21, line 51, change "4H   -1-ben-" to --4H-1-ben---;
        delete lines 54-56, and insert --dithian-2-yl]-N-methylpropylamino}propoxycarbonyl)-3-methyl-4-oxo-2-phenyl-4H-1-benzopyran,--.

UNITED STATES PATENT AND TRADEMARK OFFICE
CERTIFICATE OF CORRECTION

PATENT NO.  : 5,453,518
DATED       : September 26, 1995
INVENTOR(S) : Amedeo LEONARDI, Gianni MOTTA, Carlo RIVA and Luciano GUARNERI It is certified that error appears in the above-indentified patent and that said Letters Patent is hereby corrected as shown below:

Column 22, line 8, change "hexylamino] propylcarbamoyl}" to --hexylamino]propylcarbamoyl}--;
line 26, change "hexylamino] -1" to --hexylamino]-1--;
line 32, change "hexylamino] ethoxymethyl}" to --hexylamino]ethoxymethyl}--.

Signed and Sealed this

Second Day of July, 1996

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,453,518
DATED : September 26, 1995
INVENTOR(S) : Amedeo LEONARDI, Gianni MOTTA, Carlo RIVA and Luciano GUARNERI It is certified that error appears in the above-indentified patent and that said Letters Patent is hereby corrected as shown below:

Column 11, line 58, change "was" to --were--.

Column 17, line 67, change "." to --:--.

Signed and Sealed this

Fifth Day of November, 1996

Attest:

BRUCE LEHMAN

Attesting Officer    Commissioner of Patents and Trademarks